(12) United States Patent
Clarke et al.

(10) Patent No.: US 9,907,694 B2
(45) Date of Patent: Mar. 6, 2018

(54) INTRAOCULAR MEDICAMENT DELIVERY DEVICE

(75) Inventors: Alastair Robert Clarke, Cheshire (GB); David Heighton, Fife (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 288 days.

(21) Appl. No.: 14/129,856

(22) PCT Filed: Jun. 26, 2012

(86) PCT No.: PCT/EP2012/062285
§ 371 (c)(1),
(2), (4) Date: Dec. 27, 2013

(87) PCT Pub. No.: WO2013/000879
PCT Pub. Date: Jan. 3, 2013

(65) Prior Publication Data
US 2014/0135716 A1    May 15, 2014

(30) Foreign Application Priority Data
Jun. 30, 2011  (EP) ..................... 11172178

(51) Int. Cl.
    *A61F 2/16*   (2006.01)
    *A61L 27/18*  (2006.01)
    *A61F 9/00*   (2006.01)
(52) U.S. Cl.
    CPC ................. *A61F 9/0017* (2013.01)
(58) Field of Classification Search
    CPC ................. A61F 9/0017; A61F 2/16
    USPC ........................ 604/297, 301, 294
    See application file for complete search history.

(56) References Cited

U.S. PATENT DOCUMENTS

| 3,906,949 | A  | * | 9/1975 | Holland | A61F 9/0008 604/297 |
| 6,251,090 | B1 | * | 6/2001 | Avery | A61F 9/0017 604/294 |
| 7,695,135 | B1 | * | 4/2010 | Rosenthal | G02C 7/04 351/159.02 |
| 2006/0034890 | A1 | | 2/2006 | Roy et al. | |
| 2006/0110428 | A1 | * | 5/2006 | deJuan | A61F 9/0017 424/427 |

(Continued)

FOREIGN PATENT DOCUMENTS

| JP | 2009508587 A | 3/2009 |
| WO | 2011022484 A1 | 2/2011 |

OTHER PUBLICATIONS

Form PCT/IB/326; Notification Concerning Transmittal of International Preliminary Report on Patentability.

(Continued)

*Primary Examiner* — Tatyana Zalukaeva
*Assistant Examiner* — Sara Sass
(74) *Attorney, Agent, or Firm* — McDonnell Boehnen Hulbert & Berghoff LLP

(57) ABSTRACT

Described is a medicament delivery device comprising a body adapted to be placed on the eye and a reservoir formed in the body containing a medicament. The body has a first surface adapted to contact at least a portion of the eye and be centered around a cornea. At least one projection is formed on the first surface. The projection includes a channel adapted to create a fluid flow path for the medicament from the reservoir to a terminal end of the projection.

17 Claims, 1 Drawing Sheet

(56) References Cited

U.S. PATENT DOCUMENTS

| | | |
|---|---|---|
| 2008/0107713 A1 | 5/2008 | Orilla et al. |
| 2008/0287915 A1 | 11/2008 | Rosenthal et al. |
| 2009/0004245 A1 | 1/2009 | Orilla et al. |
| 2010/0226962 A1* | 9/2010 | Rodstrom ............. A61F 9/0017 424/427 |
| 2013/0218081 A1 | 8/2013 | Roth |

OTHER PUBLICATIONS

Notice of Reasons for Rejection issued in Japanese Patent Application No. 2014-517642 dated Nov. 22, 2016.

* cited by examiner

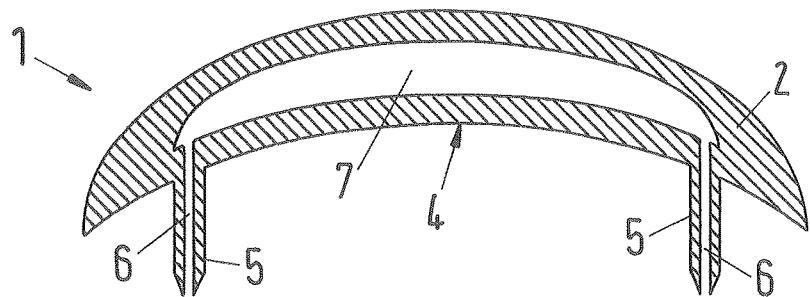
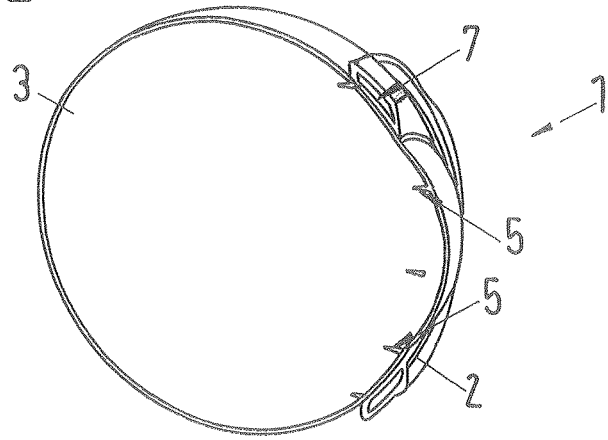
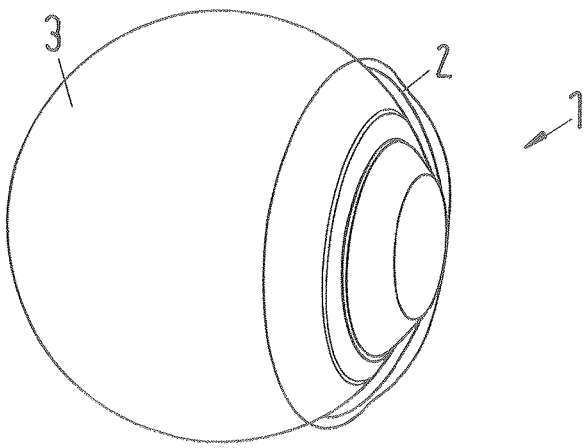

INTRAOCULAR MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2012/062285 filed Jun. 26, 2012, which claims priority to European Patent Application No. 11172178.3 filed Jun. 30, 2011. The entire disclosure contents of these applications are herewith incorporated by reference into the present application.

FIELD OF INVENTION

The present invention is directed to a medicament delivery device, and in particular a medicament delivery device for intraocular injections.

BACKGROUND

When delivering medicament to the interior, vitreous body, of the eye, the injection is planned to avoid damage to other eye structures and to target delivery of the medicament to the appropriate structure/area. Conventionally, both goals are addressed by the manual dexterity of a physician or health care provider. The physician/provider may also marking the injection site prior to insertion of the delivery device.

US 2006/0034890 A1 discloses a device for ocular delivery of medicaments to a patient through the eyelid. However, this known device is not suitable for an intraocular injection.

Therefore, there is a need for a means to facilitate intraocular injection of a medicament.

SUMMARY

It is an object of the present invention to provide a medicament delivery device requiring reduced manual dexterity on the part of the physician or health care provider, a reduced time to carry out the procedure of an intraocular injection and reducing the likelihood of complications.

In an exemplary embodiment, a medicament delivery device comprises a body adapted to be placed on an eye and a reservoir containing a medicament formed in the body. The body has a first surface adapted to contact at least a portion of the eye and be centered around a cornea. At least one projection is formed on the first surface. The projection includes a channel adapted to create a fluid flow path for the medicament from the reservoir to a terminal end of the projection.

In an exemplary embodiment, the body is a molded or cast part of a material which is similar in form to a contact lens. The body may be made of a silicone hydrogel.

In an exemplary embodiment, the projection is integrally formed with the body. The projection may be made of metal.

The medicament may be a protein, an antibody or a steroid.

In an exemplary embodiment, the body is made from a flexible material and the projection can be activated by deformation of the flexible body. For example, the projection can be activated by manual force. The medicament may be dis-pensed by manual deformation of the body or by a leaf spring.

In an exemplary embodiment, the medicament is stored within the reservoir under pressure, and the medicament may be dispensed by the fluid pressure.

BRIEF DESCRIPTION OF THE DRAWINGS

In the following, the invention will be described by a way of illustrative exemplary embodiments and with reference to the schematic drawings in which:

FIG. 1 shows a sectional view of a medicament delivery device according to an exemplary embodiment of the present invention, FIG. 2 shows a sectional view of a medicament delivery device according to an exemplary embodiment of the present invention, and FIG. 3 shows an isometric view of a medicament delivery device according to an exemplary embodiment of the present drug delivery de-vice of FIG. 2.

DETAILED DESCRIPTION

FIGS. 1-3 show exemplary embodiments of a medicament delivery device 1 adapted for intraocular injection of a medicament. In an exemplary embodi-ment, the device 1 comprises a body 2 adapted to be placed on a human eye 3. The body 2 has a first surface 4, a portion of which may contact the eye 3, and a second surface at least partially covering the first surface 4. The first surface 4 may be provided with a curvature corresponding to a contour of the eye 3. For example, a periphery of the first surface 4 may be adapted to encircle a cornea of the eye 3, and a center portion of the first surface 4 may encase (e.g., contact or without contact) the cornea. Thus, in an exemplary embodiment, the first surface 4 may be shaped and sized like a contact lens, such that the device 1 aligns itself, centered over the cornea when placed on the eye 3 due to the geometry of the first surface 4.

Those of skill in the art will understand that the first surface 4 may be made from any suitable material (e.g., silicone hydrogel) as a molded or cast part. Further, the first surface 4 may be flexible to allow deformation thereof. It may be pre-ferred to use a transparent or translucent material for the body 2. The first surface 4 may be circular or ovoid, or any other shape that would facilitate placement and/or stability of the device 1 on the eye 3 and/or administration of the medicament.

As shown in the exemplary embodiment in FIG. 1, the body 2 may include a cavity 7 to act as a reservoir for a medicament. During manufacture the reser-voir 7 may be prefilled with a medicament, e.g. steroids and/or monoclonal antibodies used to treat macular degeneration. In another exemplary embodi-ment, a port may be disposed on the body 2 which provides access to the reser-voir 7 for refilling the reservoir 7 with the medicament or another medicament (e.g., if different medicaments are used in a treatment protocol).

In an exemplary embodiment, one or more projections 5 protrude from the first surface 4 in the direction of the eye 3. In an exemplary embodiment, the projec-tions 5 may be formed on the periphery of the first surface 4. A projection 5 may be formed as a cylindrical member having a channel 6 formed therein. The channel 6 is connected to the reservoir 7 at a first end and terminates at an opening at a second end. The second end may be formed into a point to facili-tate penetration into the eye 3. While the projections 5 are depicted as being integrally formed with the body 2, those of skill in the art will understand that the projections 5 may be formed from a metal or other material different from the material used to construct the body 2.

In use, the medicament delivery device 1 is placed on the eye 3. Due to the curvature of the first surface 4 the body 2 may center itself with the cornea of the eye 3. When the body 2 is centered, the body 2 may be pressed against the eye 3 to allow the projections 5 to penetrate the eye 3. In addition, in an exem-plary embodiment, the fixed positions of the projections 5 relative to the body 2 and thus relative to the eye 3, allow for control of the angle at which the projec-tions 5 penetrate the eye 3 to minimize the chance of medicament reflux and to generally improve the rate and quality of post operative healing of the puncture site.

Penetration (activation) of the projections 5 into the eye 3 may be achieved in different ways. The projections 5 may be caused to penetrate the eye 3 by, for example, deformation of the body 2 or by manual force. On relaxation of the body 2 or on removal of the manual force, the projections 5 may revert to their start position shown in the Figures.

In an exemplary embodiment, after the body 2 has been placed on the eye 3 and the projections 5 have been introduced the eye 3, the medicament may be dispensed from the reservoir 7 by manual deformation of the body 2 or by some mechanical means (not shown), such as a leaf spring. In another exemplary embodiment, the medicament may be dispensed by having the medicament stored within the reservoir 7 under pressure. In this exemplary embodi-ment, plugs in the channels 6 may dissolve when the body 2 is placed on the eye 3. Thus, the medicament may be dispensed by the fluid pressure of the medica-ment.

While the body 2 of the medicament delivery device 1 is depicted as having a convex shape to fit to the eye 3, in another exemplary embodiment, the body 2 may be formed as an annulus.

The invention claimed is:

1. A medicament delivery device comprising:
   a body adapted to be placed on an eye, the body having a first surface adapted to contact a cornea of the eye and be centered around the cornea;
   an internal reservoir, containing a medicament, formed in the body; and
   at least one projection formed on the first surface, the at least one projection including a channel adapted to create a fluid flow path for the medicament from the reservoir to a terminal end of the at least one projection,
   wherein the at least one projection extends from the first surface towards the eye when the body is placed on the eye, and
   wherein the at least one projection penetrates the eye when the first surface is in contact with the cornea of the eye and the body is pressed toward the eye.

2. A medicament delivery device according to claim 1, wherein the body is a molded or cast part of a material which is similar in form to a contact lens.

3. A medicament delivery device according to claim 1, wherein the body is made of a silicone hydrogel.

4. A medicament delivery device according to claim 1, wherein the at least one projection is integrally formed with the body.

5. A medicament delivery device according to claim 1, wherein the at least one projection is made of metal.

6. A medicament delivery device according to claim 1, wherein the medicament is a protein, an antibody or a steroid.

7. A medicament delivery device according to claim 1, wherein the body is made from a flexible material and wherein the at least one projection can be activated by deformation of the flexible body.

8. A medicament delivery device according to claim 1, wherein the at least one projection can be activated by manual force.

9. A medicament delivery device according to claim 7, wherein the medicament is dispensed by manual deforma-tion of the body.

10. A medicament delivery device according to claim 7, wherein the medicament is dispensed by a leaf spring.

11. A medicament delivery device according to claim 7, wherein the medicament is stored within the reservoir under pressure and wherein the medicament is dispensed by a fluid pressure.

12. A medicament delivery device according to claim 1, wherein the terminal end of the at least one projection is formed as a point having an opening.

13. A medicament delivery device according to claim 1, wherein the at least one projection is cylindrical.

14. A medicament delivery device according to claim 1, further comprising a port on the body, the port being configured to provide access to the reservoir for refilling the reservoir with the medicament.

15. A medicament delivery device for delivering a medi-cament to an eye, comprising:
   a body having a first surface adapted to contact a cornea of the eye and a second surface at least partially covering the first surface;
   an internal reservoir formed in the body between the first surface and the second surface and adapted to contain a medicament;
   a projection formed on the first surface, wherein the projection extends from the first surface towards the eye when the body is placed on the eye, wherein the projection penetrates the eye when the first surface is in contact with the cornea of the eye and the body is pressed toward the eye; and
   a channel in the projection and adapted to create a fluid flow path for the medicament from the reservoir to a terminal end of the at least one projection to thereby deliver the medicament into the eye.

16. A medicament delivery device according to claim 15, wherein the projection comprises a plurality of projections.

17. A medicament delivery device according to claim 15, wherein the projection extends (i) transversely relative to the first surface and (ii) away from the first surface toward the eye when the first surface contacts the cornea.

* * * * *